United States Patent [19]

Schmidhammer et al.

[11] Patent Number: 5,177,233

[45] Date of Patent: Jan. 5, 1993

[54] CATALYST SYSTEM AND USE FOR THE PREPARATION OF 1,2-DICHLOROETHANE

[75] Inventors: Ludwig Schmidhammer, Haiming; Klaus Haselwarter, Emmerting; Hermann Klaus, Marktl; Gerhard Dummer; Klaus-Peter Mohr, both of Burghausen all of Fed. Rep. of Germany

[73] Assignee: Wacker Chemie GmbH, Munich, Fed. Rep. of Germany

[21] Appl. No.: 686,616

[22] Filed: Apr. 17, 1991

[30] Foreign Application Priority Data

Apr. 19, 1990 [DE] Fed. Rep. of Germany ....... 4012529

[51] Int. Cl.$^5$ .......................... C07F 15/02; C07F 5/06; C07F 1/00; C07F 19/00

[52] U.S. Cl. ......................................... 556/150; 556/1; 556/42; 556/51; 556/57; 556/64; 556/76; 556/80; 556/108; 556/138; 556/146; 556/181; 502/102; 502/103; 534/15

[58] Field of Search ............... 556/138, 146, 150, 180, 556/181, 1, 42, 51, 57, 64, 177, 76, 80, 81, 108; 502/102, 103; 534/15

[56] References Cited

U.S. PATENT DOCUMENTS

| | | | |
|---|---|---|---|
| 4,675,416 | 6/1987 | Brownstein | 556/138 X |
| 4,851,598 | 7/1989 | Rosenblum et al. | 556/138 X |
| 5,021,599 | 6/1991 | Beer et al. | 556/138 X |

Primary Examiner—Arthur C. Prescott
Attorney, Agent, or Firm—Burgess, Ryan & Wayne

[57] ABSTRACT

A catalyst system for the preparation of 1,2-dichloroethane by reacting ethylene and chlorine in a solvent, if desired, in the presence of an inhibitor for reducing the formation of byproducts. The catalyst system comprises a phenolate/chlorine complex. The invention also relates to a process for the chlorination of ethylene using indicated catalyst system.

7 Claims, 2 Drawing Sheets

CATALYST SYSTEM AND USE FOR THE PREPARATION OF 1,2-DICHLOROETHANE

BACKGROUND OF THE INVENTION

1) Field of the Invention

The invention relates to a catalyst system for the preparation of 1,2-dichloroethane by reacting ethylene and chlorine, if desired in the presence of an inhibitor for reducing the formation of by-products, and to a process for the preparation of 1,2-dichloroethane using this catalyst system.

2) Description of the Related Art

The preparation of 1,2-dichloroethane (EDC) by reacting ethylene with chlorine in 1,2-dichloroethane as the solvent and reaction medium is known. The catalysts used to accelerate the addition reaction of chlorine with the ethylene molecule are, besides the chlorides of elements of main groups 3 to 6 and subgroups 1,4 and 6 of the Periodic Table, in particular anhydrous iron (III) chloride, since the latter is readily accessible and inexpensive (CA-A 689991, DE-C 640827 and DE-B 1768367). The principal by-products produced in this reaction are ethyl chloride, from the competing hydrochlorination of ethylene, and, with evolution of hydrogen chloride, 1,1,2-trichloroethane as a consequence of ethylene-induced substitution of the EDC formed.

the chlorination of ethylene is frequently also carried out in the presence of oxygen as a substitution inhibitor (US-A 2601322 and DE-A 1568583).

The addition reaction of chlorine with ethylene is carried out in industry both at reaction temperatures around the atmospheric boiling point of EDC, the heat of reaction liberated being utilized to distill off and purify by rectification the reaction product and possibly also crude EDC from other origins, and at lower temperatures of from 30° to 60° C., as described in Ullmanns Encyclopädie der technischen Chemie [Ullmann's Encylclopaedia of Industrial Chemistry], Volume 9, page 427 (1975). In the latter case, however, the temperature level of the reaction is kept so low that the reaction enthalpy liberated cannot conveniently be utilized, but instead must be dissipated into the cooling water or into the air by circulating the reaction medium by pumping via a heat exchanger (DE-A 1905517).

The crude, catalyst-containing EDC prepared at lower temperatures is usually discharged from the reactor in liquid form and must be washed with acidulated water to remove the catalyst and subsequently with aqueous alkali metal hydroxide solutions in order to neutralize the crude product. The phases are separated by decanting and separating off the aqueous layer, and the water-saturated crude EDC which remains is subsequently worked up in a known manner by distillation; however, this is complex.

In DE-A 2427045, ethylene is chlorinated at temperatures of from 100° to 130° C. and appropriately high pressures in order to be able to carry out the reaction in the liquid phase, in the presence of iron(III) chloride as catalyst. The product is then fed, with the circulating reaction medium, to a zone under lower pressure, in which the crude EDC formed is evaporated by the heat of reaction liberated during the reaction of chlorine with ethylene and is rectified with recycling of high-boiling impurities into the reaction zone. The result is an accumulation of high-boiling compound sin the reaction circuit. Although this accumulation can be kept within the desired limits by batchwise removal of a liquid catalyst-containing circulation product from the bottom of the reactor, it is, however, necessary to occasionally add iron(III) chloride to the reaction medium in appropriate amounts in order to prevent catalyst depletion. In addition, disposal of the discharge from the reactor bottom presents difficulties. Moreover, the use of iron(III) chloride as catalyst at elevated reaction temperatures is also associated with certain disadvantages. Firstly, iron(III) chloride promotes, at increasing temperature, the decomposition of the formed EDC with deposition of tar-like, amorphous and carbon-rich deposits (J. Soc. Chem. Ind. 69 (1950) page 289), which causes increased formation of byproducts with increasing temperature and, in particular, a considerable decrease in the ethylene yield. Secondly, iron(III) chloride has a corrosive effect in the presence of traces of water on the materials usually used in reactor and apparatus construction, which very generally causes an overproportional increase in the rate of corrosive attack with increasing temperature.

The corrosive behavior of iron(III) chloride is further increased by hydrogen chloride, which is virtually always present due to undesired side reactions, since the highly corrosive hydrogen tetrachloroferrate complex, which very easily releases aggressive protons, is thereby formed. For this reason, attempts have been made to carry out the reaction between ethylene and chlorine completely and selectively in the absence of metal salt catalysts by adding organic catalysts, such as, for example, hydroxyl-containing aromatic compounds (DE-B 1902843). However, this only succeeds for a short time, since, in particular at elevated temperatures, chlorination of the aromatic ring occurs with time and, on the other hand, the catalystic effectiveness of organic catalysts of this type drops drastically with increasing degree of chlorination.

The process of EP-A 82342 (iron(III) chloride catalyst in the presence of nitrogen bases, such as ammonia, amines or salts of these bases) or of EP-A 111203 (alkali metal or alkaline earth metal tetrachloroferrate catalysts) can be used to considerably reduce, in particular in the medium temperature range form 90° to 120° C., the corrosion in reactors made of conventional metallic materials which is caused by iron(III) chloride as catalyst in the preparation of EDC, if the iron(III) chloride catalyst is charged with the additives mentioned therein. In addition, these additives also have an advantageous effect on the formation of byproducts, which are thereby reduced in amount. However, at elevated reaction temperatures, which are unavoidable for economical utilization of the reaction enthalpy liberated during the chlorination of ethylene, these corrosion-inhibiting and reaction selectivity-promoting effects are considerably diminished since the ammonium or alkali metal or alkaline earth metal tetrachloroferrates which form on addition of ammonium chloride or organic amine hydrochlorides or alkali metal or alkaline earth metal chlorides to iron(III) chloride, are thermally labile and decompose more and more with increasing temperature to form the starting components, from which in turn extremely corrosive hydrogen tetrachloroferrate is produced to an increasing extent in addition to the virtually inert ammonium alkali metal or alkaline earth metal chlorides, which are now present and isolated as separate species. In the case of ammonium or amine hydrotetrachloroferrate complexes, this is supplemented by the fact that the ammonium ions are Brönsted acids, which eliminate highly corrosive protons with increasing temperature with formation of amine bases.

EP-A 113287 discloses a process in which about 85% of the heat of reaction liberated during the chlorination of ethylene in the presence of iron(III) chloride at temperature of from 140° to 180° C. can be utilized to generate steam. In this process, the EDC leaving the reaction zone is cooled by heat exchange with water before further work-up or recycling into the reaction zone. Apart from the negative corrosion behavior of bare iron(III) chloride, many byproducts are also produced. However, it is certainly the more correct way industrially to utilize the reaction enthalpy liberated to generate steam or to heat a heat-transfer medium, since this is more flexible and optimum recovery of the reaction enthalpy from the chlorination of ethylene can be achieved, even in the case of "unbalanced" conditions which occur during daily events or in general.

In the process of EP-A 75742, the reaction mixture form the chlorination of ethylene is divided into two sub-streams, or which one is passed through a heat exchanger and then returns into the circuit, while the second sub-stream is depressurized and fed to a rectification column, which is heated via said heat exchanger. In this procedure, there is none of the flexibility just discussed, so that deviations from the "balanced process", due to the lack of sufficient heat of reaction to be liberated or due to production of EDC in excess of that from the "balanced process" mean that the high-boiling component column integrated into the reaction system must additionally be heated with steam or, in the reverse case, excess reaction enthalpy must be passed into the cooling water or into the air via a trim cooler. Deviations from the "balanced process" thus occur, for example, if, due to a temporary lack of chlorine, the chlorination of ethylene must be reduced or if, due to an oversupply of external hydrogen chloride, the oxychlorination of ethylene is enhanced or, in the normal direct chlorination procedure, the oxychlorination alternatively operates at a lower rate due to reduced production of vinyl chloride monomer.

The object was therefore to develop a catalyst system for the preparation of 1,2-dichloroethane which ensures the highest possible selectivity and yield in all industrially important temperature ranges, i.e. from 0° C. to 300° C., in the chlorination of ethylene, and a minimum of corrosion.

A further object was to convert this catalyst system to a simple and economical process for the preparation of EDC by chlorinating ethylene, which process makes it possible, depending on the local conditions, either to sue at least some of the reaction enthalpy liberated for isolating pure EDC of cracking quality or to utilize virtually all the reaction enthalpy liberated to generate steam at an industrially useful pressure level; the catalyst system should remain in the reaction medium, and the EDC formed need only be freed from small amounts of high-boiling impurities before being used in a pyrolysis furnace.

SUMMARY OF THE INVENTION

The invention relates to a catalyst system for the preparation of 1,2-dichlorethane by reacting ethylene and chlorine in a solvent, if desired in the presence of an inhibitor for reducing the formation of by-products, the catalyst system comprising a phenolate/chlorine complex of the formula $$Me^{+n}[Z^{+m}Cl_m \cdot L]_n$$

in which n is an integer from 1 to 3, m is an integer from 1 to 6,

Cl is a chloride anion, $Me^{30}$ is a hydrogen proton and/or a metal cation of elements from the 1st and/or 2nd main group or of the lanthanide group of the Periodic Table of the Elements (PTE), $Z^+$ is a metal cation of elements of the 3rd, 4th, 5th or 6th main group or of the 1st, 4th, 6th or 8th sub-group of the PTE, and L is a phenolate anion of the formula:

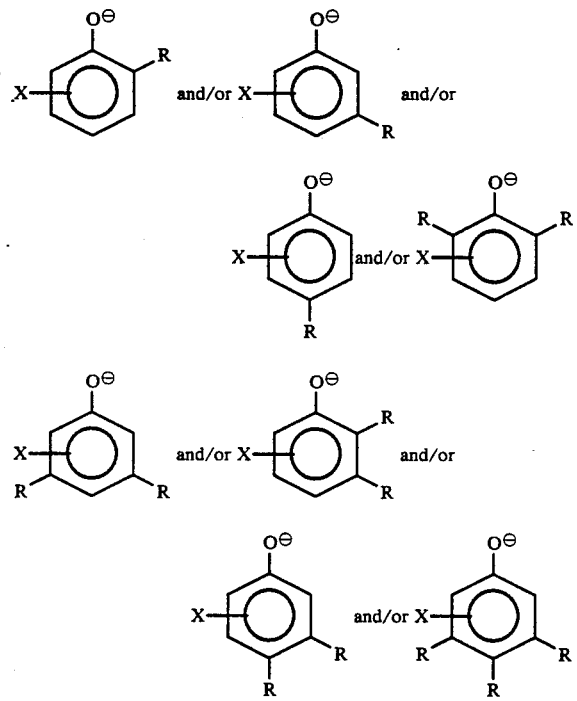

in which

X denotes 0 to 4 chlorine atoms, and

R is a hydrogen atom and/or a hydroxyl group and/or a halogen and/or a linear or branched alkyl or chloroalkyl group having from 1 to 6 C atoms and/or an alkoxy or chloroalkoxy group having 1 to 6 C atoms in a linear or branched arrangement.

DESCRIPTION OF THE PREFERRED EMBODIMENTS

Figure 1:
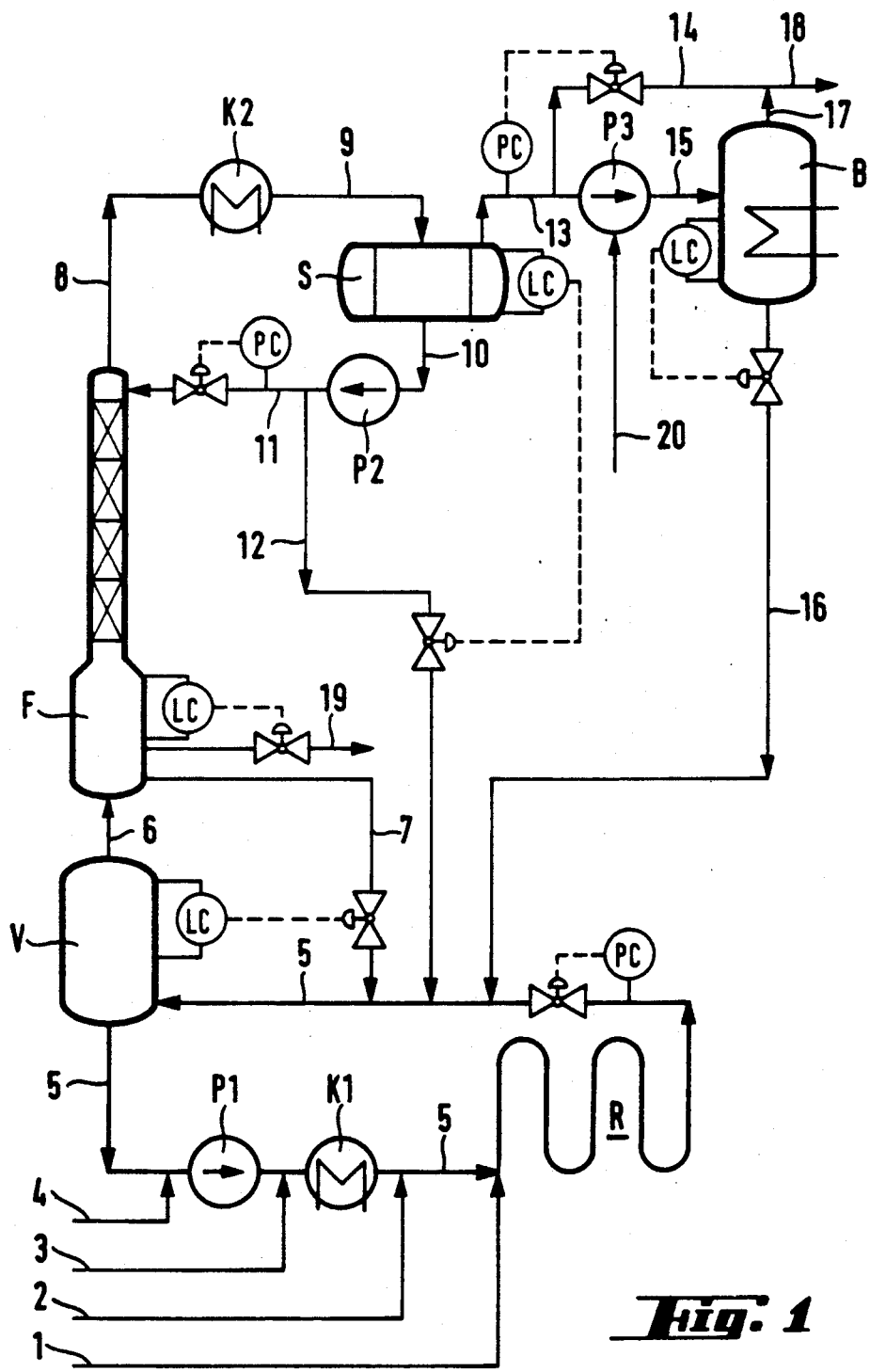
FIG. 1 is a diagram of the one embodiment of the process of the invention as set froth in Example 5.

The catalyst system according to the invention is prepared by mixing the component $Me^{+n}Cl_n$, i.e., hydrogen chloride gas and/or alkali metal chlorides and/or alkaline earth metal chlorides, or chlorides of the lanthanides with components $Z^{+m}Cl_m$, i.e., with metal chlorides of elements of the 3rd,4th,5th, or 6th main group or of the 1st,4th,6th or 8the sub-group of the Period Table of the Elements, and with the phenolic compounds of the above-described general formulae.

The admixing is carried out in each case in virtually equimolar amounts of $Z^{+m}Cl_m$ and the phenolic compound to each another, with a scattering range of in each case from 0.9 to 1.1:1 equivalent proportions, as a solution or suspension, preferably in 1,2-dichloroethane. The equivalence between $Me^{+n}Cl_n$ and the phenolic compound may also have a scattering range of in each case from 0.5 to 1.5:1, but the scattering range is preferably likewise from 0.9 to 1.1:1.

The preparation of catalysts $Me^{+n}[Z^{+m}Cl_m.L]_n$ according to the invention from the mixture of $Z^{+m}Cl_m$, $Me^{+n}Cl_n$ and the phenolic compound may be carried out in a separate reaction step by mixing and, if necessary, heating the mixture under reflux for several hours, or in situ, in the reaction zone of the ethylene chlorination reactor, after addition of the mixture to the reaction medium.

In the case of chlorinated phenolic ligands, the benzene ring chlorination can take place separately in the EDC solution before mixing with the other constituents of the catalyst system or in a separate catalyst batch mixer. The benzene ring chlorination is preferably carried out in situ in the reaction zone of the ethylene chlorination reactor after addition of the mixture of the individual catalyst components.

Preferred alkali metal and alkaline earth metal chlorides are sodium chloride and calcium chloride. The preferred lanthanide is cerium(III) chloride. The metal chlorides providing the central atom Z of the phenolate/chlorine complex are preferably aluminum chloride, tin(IV) chloride, bismuth(III) chloride, tellurium(IV) chloride, gold(III) chloride, titanium(IV) chloride, tungsten(VI) chloride, thallium(I) chloride and iron(III) chloride. Particular preference is given to iron(III) chloride. Particularly suitable phenolic compounds are phenol; ortho-, meta- and para-cresol; ortho-, meta- and para-chlorophenol; 2-sec-butylphenol, pyrocatechol, resorcinol, hydroquinone, guajacol, pyrogallol, oxyhydroquinone, phloroglucine and 3,5-di-tert-butylhydroquinone.

Particularly preferred catalyst are hydrogen meta-cresolate trichloroferrate, sodium ortho-cresolate trichloroferrate, calcium bis-para-cresolate trichloroaluminate and cerium tris-ortho-cresolate trichloroaluminate which, if desired, may be mono- or poly-chlorinated on the benzene ring.

The invention furthermore relates to a process for the preparation of 1,2-dichloroethane by reacting ethylene with chlorine, in a reaction zone which contains a circulating liquid medium comprising chlorinated hydrocarbons having 2 carbon atoms, at a temperature below the evaporation temperature of the medium, at the pressure prevailing in the reaction zone, if desired in the presence of oxygen as an inhibitor for preventing side reactions, wherein a) the concentration of the catalyst system $Me^{+n}[Z^{+m}Cl_m.L]_n$, dissolved or suspended in the reaction medium is, calculated as $Z^{+m}Cl_m$, from 0.01 to 1.0% by weight, based on the amount of reaction medium, and the catalyst system is circulated with replenishment of the consumed ethylene and chlorine, where, b) at reaction temperatures of from 0° to 300° C. and at pressures which prevent the reaction medium boiling in the reaction space, with utilization of all or some of the reaction enthalpy liberated during the chlorination of ethylene to generate 1,2-dichloroethane vapor, vaporized 1,2-dichloroethane is removed from the reaction zone into a zone of lower pressure, and these vapors are introduced into the bottom of a rectification column, and, c) at reaction temperatures of from 0° C. to 120° C., the vapors at the head of the column are condensed by cooling with water or air, at reaction temperatures of from 120° to 300° C., the heat of condensation of the vapors is utilized by heat exchange of the vapors from the rectification column with a heat-exchange medium, and, d) while maintaining a minimum reflux ratio, expressed as the ratio by weight of the reflux to the product generated, of 2:1 parts by weight in the low-temperature procedure and of 1:1 parts by weight in the high-temperature procedure, the condensed vapors are fed back into the reaction space after more or less considerable cooling in the low-temperature procedure, but after cooling by a maximum of 5° C. in the high-temperature procedure, based on the boiling or condensation temperature, and e) the 1,2-dichloroethane produced is removed in liquid form from the bottom of the rectification column.

Figure 2:
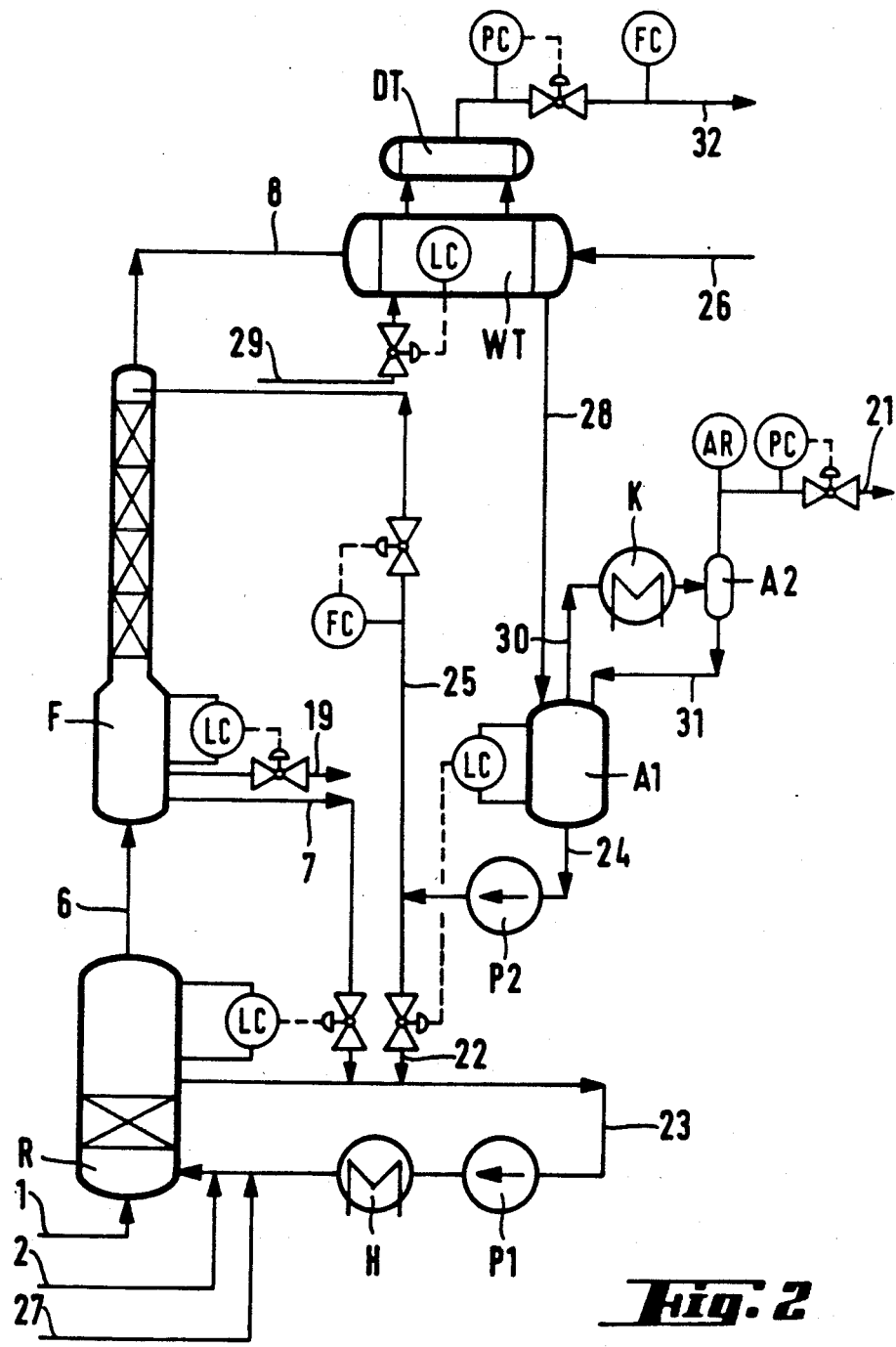
FIG. 2 is a diagram of another embodiment of the process of the invention as set forth in Example 6.

Suitable reactors for the chlorination of ethylene are loop reactors, as described, for example, in DE-A 2427045, or loop reactors as described DE-B 1768367 or in the enclosed FIG. 1, or tower reactors as described in the enclosed FIG. 2. The chlorination is carried out in a circulating liquid medium comprising chlorinated hydrocarbons having 2 carbon atoms. The reaction medium preferably employed is 1,2-dichloroethane. The speed of the circulated reaction medium is preferably between 0.1 and 5 m/s. The circulation of the liquid reaction medium in the reactor can be effected, for example, by means of a pump and/or by the thermosiphon or air-lift pump principle.

The reactor is charged with ethylene and chlorine, molar ratio between ethylene and chlorine preferably being between 1:1 and 1.005:1. The gas flow rate in the reaction space is preferably form 0.01 to 1 m/s, based on the ethylene gas stream.

The concentration of the catalyst system $Me^{+n}[Z^{+m}Cl_m.L]_n$ dissolved or suspended in the reaction medium is between 0.01 and 1.0% by weight, preferably 0.2 to 0.7% by weight, which is based in each case on the amounts of reaction medium and calculated as $Z^{+m}Cl_m$. In a preferred embodiment, the catalyst system in the form of the individual components is dissolved or suspended in the reaction medium, the individual components preferably being employed in a molar ratio of from 0.9 to 1.1:1 to one another.

Particularly preferred catalysts are hydrogen meta-cresolate trichloroferrate, sodium ortho-cresolate trichloroferrate, calcium bis-para-cresolate trichloroaluminate and cerium tris-ortho-cresolate trichloroaluminate, which may, if desired, be mono- or polychlorinated on the benzene ring.

In particular, sodium ortho-cresolate trichloroferrate, preferably in a concentration of form 0.3 to 0.5% by weight, based on the reaction medium, is employed as the catalyst system. It is preferably formed in situ, after addition of an equimolar mixture, in said equivalence range, or NaCl, $FeCl_3$ and o-cresol to the reaction medium.

The catalyst system is circulated with the reaction medium with replenishment of the consumed ethylene and chlorine.

In order to suppress side reactions, oxygen or air may be employed, if desired, as an inhibitor. The concentration is from 0.01 to 10% by volume, preferably from 0.8 to 1.5% by volume, in each case calculated as oxygen and based on the amount of chlorine gas.

The mean residence time of the reactant mixture is from 0.2 to 2 minutes, based on the empty reaction, mixing and circulation space under standard conditions (0° C. 1013 mbar). The reaction time of the reactants in the reaction space is preferably between 1.5 and 60 seconds.

The chlorination reaction is carried out at reaction temperatures between 0° and 300° C. and at pressures which prevent the reaction medium boiling in the reaction space. In the case of the low-temperature procedure, the reaction temperature is from 0° to 120° C., preferably from 40° to 80° C., and the pressure in the reaction space ire preferably between 1 and 5 bar absolute. In the high-temperature procedure, the reaction temperature is form 120° to 300° C., preferably from 140° to 170° C., and the pressure in the reaction space is preferably between 5 and 10 bar absolute.

The 1,2-dichloroethane is removed from the reaction zone into a zone or lower pressure, and the resultant vapors are introduced into a rectification column. The rectification column is preferably a packed column or a tray column. The number of theoretical trays is preferably between 1 and 5.

In the low-temperature ethylene chlorination procedure, the vapors at the head of the rectification column are condensed in a condenser by indirect heat exchange with water or air. The pressure at the column head is preferably from 0.2 to 0.9 bar abs.

Some of the condensate is introduced into the rectification column as liquid reflux, and the remainder is fed to the circulated reaction medium after more or less considerable cooling, preferably at a temperature of from about 5° to 50° C. below the boiling temperature, and fed back into the reaction space. In the low-temperature procedure, the minimum reflux ratio, expressed as the ratio by weight between the reflux and the product generated, is preferably 2:1 parts by weight. The non-condensable components of the product from the head of the rectification column are discharged into the atmosphere or fed to a combustion plant.

The 1,2-dichloroethane produced is removed from the bottom of the rectification column. The residual heat of reaction can be dissipated into the cooling water or into the air via a heat exchanger in the circuit.

In the high-temperature ethylene chlorination procedure, the vapors at the head of the rectification column are condensed in a heat exchanger. The pressure at the column head is preferably from 4.5 to 8.3 bar abs. Feasible heat-exchange media are any heat carriers, for example mineral oils, which release the adsorbed heat elsewhere and, accordingly cooled, are fed back to the heat exchanger. The heat of condensation of the vapors is preferably utilized to generate saturated steam at a pressure of from 2.25 to 6.0 bar abs., by heat exchange of the vapors from the rectification column with hot water of appropriate pressure.

Some of the condensate is introduced into the rectification column as liquid reflux, and the remainder is fed to the circulated reaction medium and fed back into the reaction space; the temperature of the vapor condensate fed back into the reaction space should be cooled by a maximum of 5° C., based on the boiling or condensation temperature. In the high-temperature procedure, the minimum reflux ratio, expressed as the ratio by weight of reflux to generated product, is preferably 1:1 parts by weight. The non-condensable components of the product from the head of the rectification column are discharged into the atmosphere or fed to a combustion plant. The 1,2-dichloroethane produced is removed from the bottom of the rectification column.

By means of the process according to the invention, the reaction enthalpy liberated during the chlorination of ethylene can, in the low-temperature procedure, be utilized to the extend of at least 40% in the generation of the vapor-form 1,2-dichloroethane by depressurizing the reaction product from the chlorination of ethylene.

In the high-temperature procedure according to the invention, it is possible to recover all the reaction enthalpy liberated during the chlorination of ethylene. All the heat of reaction is utilized to generate vaporized 1,2-dichloroethane by depressurizing the reaction product and can be recovered as heat of condensation of the vapors by heat exchange.

The process according to the invention and an apparatus for the chlorination of ethylene by the low-temperature procedure are represented by way of example in FIG. 1 and Example 5. FIG. 2 and Example 6 describe the process according to the invention and an apparatus for the high-temperature procedure by way of example.

Compared with the procedures known from the prior art, the process according to the invention offers a number of advantages:

The removal of the reaction product from the reaction space in vapor form means that it is not necessary to top up the catalyst or remove the catalyst from the crude product. This is also the reason for the omission of the environmentally appropriate pretreatment of the washing water contaminated by EDC (for example removal of chlorohydrcarbon by steam stripping). The process gives high yields and extremely low formation of byproducts (high selectivity). Since the catalyst system according to the invention is virtually noncorrosive, meaning that exotic materials are not necessary and, in addition, the reaction apparatus is relatively simple and non-extensive, the apparatus costs are low, even for the high-temperature procedure. Since the EDC produced in the low-temperature procedure is already of cracking quality without additional purification steps, energy can be saved for the distillative purification of the EDC produced. The reaction enthalpy of the chlorination of ethylene can be recovered virtually quantitatively, in the form of saturated steam having a technically and economically interesting steam tension; in the high-temperature procedure with additionally reduced energy consumption for the distillative purification of the EDC produced, since the latter is free from low-boiling constituents. The procedure according to the invention gives the greatest possible flexibility between direct chlorination and oxychlorination of ethylene, corresponding to the boundary conditions prevailing in each case, with optimum energy utilization or energy saving in the process of the preparation of vinyl chloride.

Surprisingly, it has also become apparent that the catalyst system according to the invention is clearly superior to all the catalyst mixtures known hitherto for the direct chlorination of ethylene, both with respect to selectivity and with respect to corrosion behavior, this superiority becoming very clearly apparent, in particular, at elevated reaction temperatures. Thus, even in the high-temperature procedure, virtually no ethyl chloride is formed, and also significantly less 1,1,2-trichloroethane is formed than, for example, in DE-A 3148450 and European Patent 111203. Due to the fact that the catalyst system according to the invention is substantially less corrosive, both in the low-temperature and high-temperature procedures, than comparable catalyst mixtures of the prior art, it can be seen that the catalyst system according to the invention must, surprisingly, be very thermally stable.

The examples below serve to further illustrate the invention:

EXAMPLE 1

Corrosion experiments were carried out at 84° C. (boiling point of EDC) and at 212° C. (boiling point of hexachlorobutadiene) using various catalyst mixtures. To this end, V4A stainless-steel plates measuring 40×20×2 mm were in each case immersed in liquid EDC or hexachlorobutadiene. The liquid in each case contained 5000 ppm by weight of iron(III) chloride or an equimolar mixture of ammonium chloride and iron-(III) chloride or an equimolar mixture of sodium chloride and iron(III) chloride or an equimolar mixture of ortho-cresol and iron(III) chloride or an equimolar mixture of sodium chloride, ortho-cresol and iron(III) chloride, in each case in a concentration of 5000 ppm by weight, calculated as iron(III) chloride, in dissolved or suspended form. After refluxing for 24 hours in each case whilst simultaneously passing dry hydrogen chloride gas into the mixture, the corrosion rates were determined gravimetrically by differential weighing of the plates. The results are shown in Table 1.

TABLE 1

| Catalyst system | Weight loss in mg/mm².a | |
|---|---|---|
| | at 84° C. | at 212° C. |
| FeCl₃ or HFeCl₄ | 0.123 | 19.630 |
| NH₄FeCl₄ | 0.062 | 9.985 |
| NaFeCl₄ | 0.055 | 8.835 |
| H—FeCl₃.o-cresolate | 0.034 | 2.803 |
| Na—FeCl₃.o-cresolate | 0.025 | 2.020 |

The results illustrate the superiority of the catalyst system according to the invention over the prior art with respect to corrosion behavior. Thus a corrosion rate of 2 mg/mm².a, corresponds, for example, approximately to a corrosion rate of 0.25 mm/a. A corrosion rate of <1 mm/a generally means that there are no material problems with respect to service life. By contrast, the catalyst systems ammonium tetracholoroferrate and sodium tetrachloroferrate give corrosion rates at 212° C. of >1 mm/a, which means that material problems exist here with respect to service life. These results are all the more surprising if the catalyst complex H-FeCl₃ o-cresolate is considered separately. It would be known to any person skilled in the art that protonolysis of this complex, and thus the corrosion rate, increases with the temperature. However, the opposite occurred, which clearly supports the experimental results.

EXAMPLE 2

Preparation of the catalyst system NaFeCl₃ o-cresolate 5 g (31 mmol) of anhydrous iron(III) chloride were dissolved or suspended in 500 cm³ of EDC in a glass flask, and 1.8 g (31 mmol) of sodium chloride and 3.3 g (31 mmol) of o-cresol were added. The mixture was then refluxed. The hydrogen chloride which formed was removed by means of a gentle stream of nitrogen passed through the flask, and was absorbed in water. After 15 hours, 0.7 l of hydrogen chloride had been liberated, determined by titration of the washing water, i.e. the complex

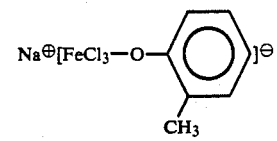

had been formed.

Chlorine gas was subsequently passed in at around 50° to 60° C. until the evolution of hydrogen chloride ceased. 3 l of hydrogen chloride were liberated, i.e. the benzene ring chlorination of the complex was complete:

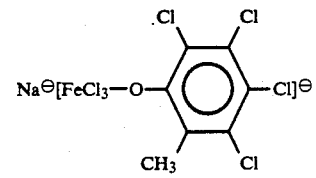

EXAMPLE 3

The vertical glass reaction tower (internal diameter 50 mm, height 300 mm) was packed with 2-mm Raschig rings and surrounded by a twin jacket in which thermostatic water was circulated at a temperature of 84° C. This additional heating was necessary, in spite of the exothermic reaction between chlorine and ethylene, to cover the heat loss due to radiation (unfavorable ratio between surface area and heat liberation), so that EDC was distilled off form the reactor. Reaction liquid at a rate of 0.6 cm/s in an amount of 40 l hr was circulated by means of a metering pump through the reactor packed with glass Raschig rings. 40 l (S.T.P.)/hr of chlorine and 250 cm³ (S.T.P.)/h of oxygen were passed into the circulating reaction medium and 40.2 l (S.T.P.)/hr of ethylene were blown into the reactor from below via a glass frit located in the reaction tower.

The reactor was in each case charged with 500 cm³ of EDC containing various catalyst systems, prepared as in Example 2, in dissolved or suspended form in a concentration of 0.5% by weight, calculated as the metal chloride which forms the central atom of the particular catalyst complex. The EDC distilled off was condensed in a water condenser and collected. 175 g/hr of EDC produced were diverted off using a condensate divider and removed, while excess condensate was fed back into the reaction zone. A further portion of EDC was removed from the offgas stream—essentially oxygen, excess ethylene and nitrogen, which was fed in in an amount of 2 l (S.T.P.)/hr after the condenser for inertization—by means of a cold trap. The combined EDC produced was analyzed for purity by gas chromatography. The offgas from the cold trap was likewise analyzed for low-boiling byproducts by gas chromatography and chlorine. Chlorine was not found in any of the experiments, i.e. the conversion was always quantitative;.

The following catalyst systems were investigated:

A) HFeCl$_3$-m-cresolate, prepared by adding equimolar amounts of iron(III) chloride and m-cresol B) NaFeCl$_3$-o-cresolate, prepared by adding equimolar amounts of NaCl, FeCl$_3$ and o-cresol C) Ca[FeCl$_3$-p-cresolate]$_2$, prepared by adding equivalent amounts of CaCl$_2$ and of the equimolar mixture of FeCl$_3$ and p-cresol D) NaFeCl$_4$-phenolate, prepared by adding equimolar amounts of NaCl, FeCl$_3$ and phenol E) NaBiCl$_3$-resorcinate, prepared by adding equimolar amounts of NaCl, BiCl$_3$ and resorcinol F) Ce[AlCl$_3$-o-cresolate]$_3$, prepared by adding equivalent amounts of CeCl$_3$ and of the equimolar mixture of AlCl$_3$ and o-cresol G) HFeCl$_4$, prepared by adding FeCl$_3$, HCl is produced during the reaction H) NH$_4$FeCl$_4$, prepared by adding equimolar amounts of NH$_4$Cl and FeCl$_3$ I) KFeCl$_4$, prepared by adding equimolar amounts of KCl and FeCl$_3$ The results are shown in Table 2. The experimental duration was 24 hours in each case.

TABLE 2

| Catalyst system | Distillate Ethyl chloride | 1,1,2-trichloro-ethane | Reaction medium 1,1,2-trichloro-ethane |
|---|---|---|---|
| A | <1 ppm by weight | 550 ppm by weight | 0.09 % by weight |
| B | <1 ppm by weight | 290 ppm by weight | 0.06 % by weight |
| C | <1 ppm by weight | 310 ppm by weight | 0.08 % by weight |
| D | <1 ppm by weight | 350 ppm by weight | 0.08 % by weight |
| E | <1 ppm by weight | 380 ppm by weight | 0.075 % by weight |
| F | <1 ppm by weight | 480 ppm by weight | 0.086 % by weight |
| G | 650 ppm by weight | 2500 ppm by weight | 0.53 % by weight |
| H | 18 ppm by weight | 850 ppm by weight | 0.10 % by weight |
| I | 25 ppm by weight | 1430 ppm by weight | 0.22 % by weight |

The results of Experiments A to F clearly demonstrate the superiority of the catalyst systems according to the invention over the prior art (Experiments G to I) with respect to selectivity. In particular, the absence of ethyl chloride is important since as is known, it forms butadiene on pyrolysis of EDC.

EXAMPLE 4

The procedure was analogous to Example 3. The following catalyst systems were prepared in situ by mixing in the experimental apparatus, in a concentration of in each case 0.4% by weight, calculated as FeCl$_3$:

A) 1 mol of FeCl$_3$ and 0.9 mol of o-cresol
B) 1 mol of FeCl$_3$ and 1.1 mol of o-cresol
C) 1 mol of FeCl$_3$ and 0.5 mol of o-cresol
D) 1 mol of FeCl$_3$ and 2 mol of o-cresol
E) 1.5 mol of NaCl, 1 mol of FeCl$_3$ and 0.9 mol of o-cresol
F) 0.5 mol of NaCl, 1 mol FeCl$_3$ and 1.1 mol of o-cresol.

The results are shown in Table 3.

TABLE 3

| Catalyst system | Distillate composition Ethyl chloride | 1,1,2-trichloroethane |
|---|---|---|
| A | <1 ppm by weight | 530 ppm by weight |
| B | <1 ppm by weight | 560 ppm by weight |
| C | 480 ppm by weight | 2300 ppm by weight |
| D | 530 ppm by weight | 2150 ppm by weight |
| E | <1 ppm by weight | 610 ppm by weight |
| F | <1 ppm by weight | 520 ppm by weight |

It can be seen from the results that a molar ratio between FeCl$_3$ and o-cresol with a scattering range of from 0.9 to 1.1:1 is important for the selectivity, but the alkali metal chloride or alkaline earth metal chloride content is less crucial, even outside the amount equivalence to FeCl$_3$. Nevertheless, the amount equivalence of the alkali metal or alkaline earth metal chlorides should be observed if at all possible since amounts above the respective equivalence can give considerable erosion problems as an inert material.

EXAMPLE 5

As shown in FIG. 1, 50 m$^3$/hr of EDC were circulated via line 5, the empty loop reactor R, the pump tank V and the water condenser K1 with the aid of the circulating pump P1.

The circulation system was charged via line 4 with equimolar amounts of FeCl$_3$, NaCl and o-cresol in a concentration of 0.5% by weight, calculated as FeCl$_3$ and based on the amount of circulating EDC.

Chlorine was reacted with ethylene at a reactor temperature of 70° C. and a pressure of 3 bar absolute by feeding 45.1 m$^3$ (S.T.P.)/hr of ethylene in via line 1, 45 m$^3$ (S.T.P.)/hr of evaporated liquid chlorine via line 2 and 500 l (S.T.P.)/hr of oxygen via line 3.

The diameter of the reactor was 100 mm and the length of the reaction tube was 1,600 mm. Some of the heat of reaction liberated was diverted off to generate EDC vapor in the pump tank V, where a pressure of about 0.67 bar absolute prevailed, and the remainder of the heat of reaction was dissipated into the cooling water in condenser K1 in order to keep the reaction temperature in the reactor R constant at 70° C. The pressure was kept constant at 3 bar absolute in the reaction part via a pressure regulator PC. 250 kg/hr of EDC evaporated at a temperature of 70° C. via line 6 into the bottom of the rectification column F, which was packed to a level of 2000 mm with ½ inch ceramic rings. Bottom product from the rectification column F flowed, depending on the level in the pump tank V, via line 7. The vapors leaving the head of the rectification column in an amount of 650 kg/hr flowed via line 8 into the condenser K2 and they were condensed. The condensate produced flowed via line 9 into the collector S and from there was fed via lines 10 and 11 with the aid of the pump P2 in an amount of 400 kg/hr kept constant by a flow controller FC, to the column F as liquid reflux, while the remainder of the distillate (about 51.5 kg/hr) was pumped, depending on the level in the collector S, and regulated via line 12, into the circulation system 5.

In the bottom of the rectification column F, the EDC produced was removed, under level control, via line 19 in an amount of 198.5 kg/hr.

The non-condensable constituents, essentially ethylene, oxygen and nitrogen, which was fed in at the gas-outlet connector of the collector S (not shown in the drawing), flowed via line 13, kept at a pressure of 0.66 bar bar absolute by PC, into the liquid ring pump P3, operating with EDC as the operating medium and produced the necessary underpressure of about 0.66 bar, measured in absolute terms, in the gas line 13. The offgas escaped at 18 via line 14 into the atmosphere or into a combustion plant.

Fresh EDC could be introduced via line 20. Consumed EDC, carrying a low content of gases, was discharged via line 15 into the water-cooled tank B, which was vented to the offgas line 14 via line 17, buffered and released into the reaction system under level control via line 16.

The EDC produced had the following quality:

| Ethyl chloride | <1 ppm by weight |
|---|---|
| 1,1,2-Trichloroethane- | 120 ppm by weight |
| 1,2-Dichloroethane | 99.98 ppm by weight |

This EDC could be reacted directly, without further purification, in a cracking furnace to give vinyl chloride and hydrogen chloride without the cracking kinetics or the formation of byproducts and coke being impaired in any way, as an operating trial had proved, after prior collection of appropriate amounts of this EDC prepared by the process according to the invention. Even after a 4-months' trial, there were no quality problems for the EDC produced nor loss of catalyst. Neither was accumulation of high-boiling components in the reactor circuit observed.

EXAMPLE 6

The reactor R as shown in FIG. 2 comprised a vertical, packed tower (diameter 200 mm, height 4000 mm). 50 m³/hr of EDC were circulated by means of the pump P1 via line 23 and the heat exchanger H, which was heatable by steam, n order to make the entire apparatus water-free by azeotropic distillation with EDC. This circulation stream contained dissolved or suspended FeCl₃, NaCl and m-cresol in equimolar amounts to one another and in a concentration of 0.5% by weight, calculated as FeCl₃.45.2 m³ (S.T.P.)/hr of ethylene were introduced via line 1, 45 m³ (S.T.P.)/hr of chlorine as liquid chlorine via line 2 and 400 l (S.T.P.)/hr of oxygen via line 27. The reaction between ethylene and chlorine was carried out at 165° C. and a pressure of 7.3 bar absolute, the heat of reaction liberated being used to generate EDC vapor. 1345 kg/hr of EDC evaporated at a pressure of about 7.1 bar via line 6 into the bottom of the rectification column F, which was packed to a level of 2000 mm with ½ inch ceramic rings. 1545 kg/hr of EDC vapors at a temperature of about 162° C. flowed via line 8 into the steam generator WT, in which, with condensation of the vapors and with level control, boiler feed water at 150° C. fed in via line 29 in an amount of 200 kg/hr measured by the flow meter FQ, was accordingly converted into saturated steam at a pressure of 4.9 bar absolute, which, after phase separation in the steam drum DT under pressure control, was released into the steam network via line 32. Nitrogen was introduced at 26 for inertization purposes. The condensed vapors flowed via line 28 into the separator A1, from where they were introduced into the column F as liquid reflux via line 24 with the aid of the pump P2, fixed value-regulated via FC, and line 25 in an amount of 200 kg/hr or pumped into the circulation system under level control via line 22. The non-condensable offgas flowed to the condenser K via line 30, and any condensate produced was collected in the separator A2 and flowed back to the separator A1 via line 31. The offgas was released into the open or fed to a combustion plant under pressure control at 7.05 bar absolute at 21.

The offgas was analyzed for chlorine using the analyzer AR. Bottom product from the column F was diverted into the reaction system via line 7, regulated by the level in the reaction tower. Chlorine was not found in the analyzer AR, i.e. the conversion of chlorine was quantitative.

198.5 kg/hr of EDC produced were removed via line 19 under level control. The EDC produced had the following composition:

| Ethyl chloride | <1 ppm by weight |
|---|---|
| 1,1,2-Trichloroethane | 3100 ppm by weight |
| 1,2-Dichloroethane | 99.68 ppm by weight |

Due to the relatively high level of 1,1,2-trichloroethane, the crude EDC had to be freed from these high-boiling components in a conventional manner before being used for thermal cracking to give vinyl chloride and hydrogen chloride.

Even after an experimental duration of 3 months, no catalyst deactivation or depletion had occurred, i.e. the catalyst system according to the invention as thermally stable.

What is claimed is:

1. A catalyst system useful for the preparation of 1, 2-dichloroethane from ethylene and chlorine, said catalyst system comprising a phenolate/chlorine complex of the formula

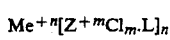

$$Me^{+n}[Z^{+m}Cl_m.L]_n$$

wherein n is an integer from 1 to 3 m is an integer from 1 to 6

Cl is a chloride anion,

Me+ is a hydrogen proton and a metal cation of elements of the 1st and 2nd main group or of the lanthanide group of the Periodic Table of the Elements, Z+ is a metal cation of elements of the 3rd, 4th, 5th or 6th main group or of the 1st,4th,6th or 8th subgroup of the Periodic Table of the Elements, and L is at least one phenolate anion selected from the group consisting of

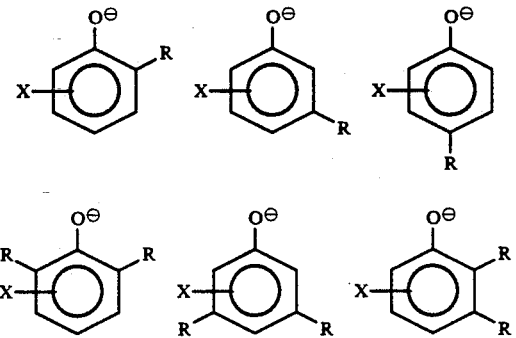

-continued

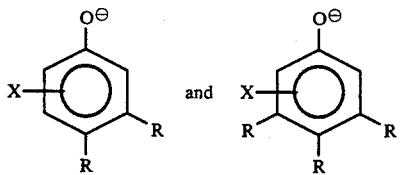

wherein X denotes hydrogen or up to 4 chlorine atoms, and R is at least one member selected from the group consisting of hydrogen, hydroxyl, halogen, and linear or branched alkyl, chloroalkyl, alkoxy and chloroalkoxy of 1 to 6 carbon atoms, and wherein the R's need not be the same in the same anion.

2. A catalyst system as claimed in claim 1, which is selected from the group consisting of hydrogen meta-cresolate trichloroferrate, sodium ortho-cresolate trichloroferate, calcium bis-paracresolate trichloroaluminate and cerium tris-ortho-cresolate trichloroaluminate.

3. A catalyst system as claimed in claim 1, wherein the catalyst system is prepared by mixing the compounds $Z^{+m}Cl_m$, $Me^{+n}Cl_n$ and the phenolic compounds L in equivalent amounts, the equivalence between $Z^{+m}Cl_m$ and the phenolic compound L having a scattering range of in each case from 0.9 to 1.1:1 equivalent proportions, and the equivalence between $Me^{+n}Cl_n$ and the phenolic compounds L having a scattering range of in each case from 0.5 to 1.5:1 equivalent proportions.

4. A catalyst system as claimed in claim 1 or 3 wherein the equivalence between $Me^{+n}Cl_n$ and the phenolic compound L has a scattering range of in each case from 0.9 to 1.1:1 equivalent proportions.

5. A catalyst system as claimed in claim 1, 2, 3 or 4 wherein the preparation is carried out by mixing hydrogen chloride, meta-cresol and iron(III) chloride.

6. A catalyst system as claimed in claim 1, 2, 3 or 4 wherein the preparation is carried out by mixing sodium chloride, ortho-cresol and iron(III) chloride.

7. A catalyst system as claimed in claim 1, 2, 3 or 4 wherein the preparation is carried out by mixing calcium chloride, para-cresol and aluminum chloride.

* * * * *